United States Patent
Uppara et al.

(10) Patent No.: US 9,029,575 B2
(45) Date of Patent: May 12, 2015

(54) PROCESS FOR PREPARATION OF ACETALS

(71) Applicant: Reliance Industries Limited, Mumbai, Maharashtra (IN)

(72) Inventors: Parasu Veera Uppara, Maharashtra (IN); Pavankumar Aduri, Maharashtra (IN); Mangesh Sakhalkar, Maharashtra (IN); Uday Ratnaparkhi, Maharashtra (IN)

(73) Assignee: Reliance Industries Limited, Mumbai (IN)

( * ) Notice: Subject to any disclaimer, the term of this patent is extended or adjusted under 35 U.S.C. 154(b) by 0 days.

(21) Appl. No.: 13/936,393

(22) Filed: Jul. 8, 2013

(65) Prior Publication Data

US 2013/0296580 A1 Nov. 7, 2013

Related U.S. Application Data

(63) Continuation of application No. PCT/IN2011/000120, filed on Feb. 28, 2011.

(30) Foreign Application Priority Data

Jan. 10, 2011 (IN) .............................. 78/MUM/2011

(51) Int. Cl.
 C07D 493/00 (2006.01)
 C07D 493/04 (2006.01)
 C07H 9/04 (2006.01)

(52) U.S. Cl.
 CPC ................ *C07D 493/04* (2013.01); *C07H 9/04* (2013.01)

(58) Field of Classification Search
 CPC .................................................... C07D 493/04
 USPC ........................................................ 549/364
 See application file for complete search history.

(56) References Cited

U.S. PATENT DOCUMENTS

| | | | |
|---|---|---|---|
| 3,721,682 A | 3/1973 | Murai et al. | |
| 4,267,110 A | 5/1981 | Uchiyama | |
| 4,429,140 A | 1/1984 | Murai et al. | |
| 4,562,265 A | 12/1985 | Machell | |
| 4,902,807 A | 2/1990 | Kobayashi et al. | |
| 5,023,354 A | 6/1991 | Salome et al. | |
| 5,104,840 A | 4/1992 | Chauvin et al. | |
| 5,731,474 A | 3/1998 | Scrivens et al. | |
| 5,892,124 A * | 4/1999 | Olivier et al. ................. | 568/324 |
| 6,500,964 B2 | 12/2002 | Lever et al. | |
| 6,527,977 B2 | 3/2003 | Helber et al. | |
| 6,573,405 B1 | 6/2003 | Abbott et al. | |
| 7,183,433 B2 | 2/2007 | Abbott et al. | |
| 7,196,221 B2 * | 3/2007 | Abbott et al. ................. | 564/282 |
| 2002/0137953 A1 | 9/2002 | Lever et al. | |
| 2005/0147889 A1 | 7/2005 | Ohzuku et al. | |
| 2006/0183654 A1 | 8/2006 | Small | |
| 2008/0221353 A1 | 9/2008 | Tsunashima | |
| 2008/0307703 A1 | 12/2008 | Dietenberger et al. | |
| 2009/0247432 A1 | 10/2009 | Miller | |
| 2012/0232150 A1 | 9/2012 | Mobashery et al. | |

FOREIGN PATENT DOCUMENTS

| | | |
|---|---|---|
| CN | 1858048 | 11/2006 |
| CN | 1903857 | 1/2007 |
| CN | 101440025 | 5/2009 |
| CN | 101544628 | 9/2009 |
| CN | 101723852 | 6/2010 |
| JP | 2009057297 | 3/2009 |
| KR | 1020080003855 | 1/2008 |
| WO | WO00/41809 | 7/2000 |
| WO | 02/26701 | 4/2002 |
| WO | WO2006/007703 | 1/2006 |
| WO | 2006/044187 | 4/2006 |
| WO | WO2007/023814 | 3/2007 |
| WO | WO2012/095858 | 7/2012 |

OTHER PUBLICATIONS

International Search Report of PCT/IN2011/000120, dated Oct. 20, 2011, 3 pages.
Olivier-Bourbigou, H., et al., Applied Catalysis A: General, 373, 1-56, 2010.
Deetlefs, M., et al., Liquid Structure of the Ionic Liquid 1, 3-Dimethylimidazolium Bis,, J. Physical Chemistry B. 110, 12055-12061, 2006.
Canongia Lopez, J. N. and A. A. H.Padua, Nanostructural Organization in Ionic Liquids , J. Physical Chemistry B. 110, 3330-3335, 2006.
Angew. Chem. Int. Ed., Ionic Liquids—New "Solutions" for Transition Metal Catalysis, 2000, 39, 3772-3789.
International Search Report of PCT/IN2011/000123, dated Oct. 27, 2011, 3 pages.
Office Action for U.S. Appl. No. 13/936,436 issued on Oct. 9, 2013.
International Search Report of PCT/IN2011/000122, dated Oct. 20, 2011, 4 pages.
Non-Final Office Action for U.S. Appl. No. 13/978,579, dated Jun. 19, 2014, 8 pages.

\* cited by examiner

*Primary Examiner* — Andrew D Kosar
*Assistant Examiner* — Raymond Covington
(74) *Attorney, Agent, or Firm* — Collard & Roe, P.C.

(57) ABSTRACT

A process for the preparation of 1,3:2,4-bis(4-methylbenzylidene)sorbitol (MDBS) and 1,3:2,4-bis(3,4-dimethylbenzylidene)sorbitol (DMDBS) via a dehydrocondensation reaction is disclosed. The reaction is carried out between an aldehyde and an alditol in a mole ratio of 2:1 wherein ionic fluid is used as the acidic catalyst and/or reaction medium. The ionic fluid used in accordance with the present invention is quaternary ammonium salt based ionic liquid.

15 Claims, No Drawings

US 9,029,575 B2

PROCESS FOR PREPARATION OF ACETALS

CROSS REFERENCE TO RELATED APPLICATIONS

This application is a continuation application of International Application Ser. No. PCT/IN2011/000120 filed Feb. 28, 2011 which claims priority under 35 U.S.C. 119 of Indian Application 78/MUM/2011 filed on Jan. 10, 2011 the disclosures of which are hereby incorporated herein by reference in their entirety. The international application under PCT article 21(2) was published in English

FIELD OF THE INVENTION

The present invention relates to a process for the preparation of 1,3:2,4-bis(4-methylbenzylidene) sorbitol (MDBS) and 1,3:2,4-bis(3,4-dimethylbenzylidene) sorbitol (DMDBS). Particularly, the present invention relates a process for preparation of MDBS and DMDBS using an ionic fluid.

BACKGROUND OF THE INVENTION

The acetal compound is the reaction product of an alditol and benzaldehyde. Alditol acetals, such as MDBS (1,3:2,4-bis(4-methylbenzylidene)sorbitol) and DMDBS (1,3:2,4-bis(3,4-dimethylbenzylidene)sorbitol) derivative compounds are known compounds which find their utility as an additive in polypropylene. Acetals of substituted and unsubstituted aldehydes are also known to be useful as nucleating agents, gelling agents, processing aids, and strength modifiers in polyolefin resins, polyester resins, deodorant, and antiperspirant compositions; hydrocarbon fuels and paints.

Acetal-alditols are typically prepared by the condensation reaction of an aromatic aldehyde with an alditol containing 6 carbon atoms like sorbitol. For MDBS and DMDBS structures, such reactions involve two moles of the aldehyde and one mole of an alditol.

Several methods for the preparation of acetal-alditols have been reported in U.S. Pat. No. 4,267,110, U.S. Pat. No. 3,721,682, U.S. Pat. No. 4,429,140; U.S. Pat. No. 4,562,265; U.S. Pat. No. 4,902,807; U.S. Pat. No. 5,023,354; U.S. Pat. No. 5,731,474 and U.S. Pat. No. 6,500,964.

The hitherto reported methods suffer from several shortcomings. Majority of the earlier known processes employ various organic solvents which necessitates high temperature for carrying out the reaction thereby increasing the cost component. Furthermore, most of the solvents are very expensive and they too render the process un-economical.

Attempts have been made in the past to overcome the above mentioned shortcomings by employing the acidic catalyst for improving the yield and the versatility (ability to employ variety of substituted aldehydes) the process.

The presently known processes for the preparation of acetals which employ acidic catalysts still suffer from several limitations. Though mineral acids serve as good catalysts for the acetalization process, they are very corrosive in nature. Furthermore, the final product resulting from such processes needs to be purified by neutralizing the residual free acid. Though the yields offered by all teachings are acceptable for the practical purposes, all the methods are not effective from the perspective of versatility, environmentally friendliness, energy efficient, reliability, cost-effective, and safe production.

Ionic systems, which are examples of viscous molten salts, have a number of interesting and useful properties, and have utility, for example, as highly polar solvents, co-solvents and catalyst in synthetic chemistry. They also have been found to be useful in applications in various fields such as electrochemistry, synthesis of chemical compounds, dyes, batteries, fuel cells, photovoltaic devices, electro-deposition processes, semi conductor cleaning, pyrolysis, gasification, in applications involving cellulose dissolution, for the electroplating of metals as described, for example in U.S. Pat. No. 6,573,405, U.S. Pat. No. 7,183,433, U.S. Pat. No. 7,196,221, U.S. Patent Appl. No. 2005/0147889, U.S. Pat. No. 6,527,977, U.S. Pat. Appl. No. 2008/0307703, U.S. Pat. Appl. No. 2006/0183654, U.S. Pat. Appl. No. 2009/0247432.

Ionic liquids exhibit very low or no vapour pressure and thus, in contrast to many conventional molecular solvents produce virtually no vapours. They are therefore advantageous from a health, safety and environmental point of view.

Ionic fluids prepared from quaternary ammonium salt as one of the ions have been reported in U.S. Pat. No. 5,892,124, U.S. Pat. No. 5,104,840, U.S. Pat. No. 6,573,405, U.S. Pat. No. 7,183,433 and U.S. Pat. No. 7,196,221.

Ionic compound taught in U.S. Pat. No. 7,183,433 is prepared by mixing a quaternary amine salt of formula $R1R2R3R4N^+X^-$ with a hydrogen bond donor. For example, a viscous ionic compound is prepared by mixing 0.1 mole of choline chloride and 0.1 mole of para toluene sulfonic acid. The reaction is generally endothermic, and is usually carried out by heating.

The method taught in U.S. Pat. No. 7,183,433 suffers from several limitations. Firstly, the process taught in U.S. Pat. No. 7,183,433 needs energy and secondly it is very time consuming and tedious because of the viscous nature of the end product.

Processes for preparation of acetals and di-acetals other than MDBS and DMDBS structures using ionic liquids as catalysts and/or reaction medium have been reported. For example, CN 101440025 discloses a method for preparation of ethylidene ether or ketal which employs N-methyl glyoxaline bisulphate ionic liquid catalyst. Other patents which disclose the use of ionic liquids as catalyst for preparation of acetals other than MDBS and DMDBS structures include CN 101723852, CN 101544628 and CN 1858048.

None of the hitherto reported processes for preparation of MDBS and DMDBS have employed ionic liquids as catalysts and/or reaction medium. There exists a need for process for preparation of MDBS and DMDBS which uses ionic liquids as the catalyst and or reaction medium. There also remains a need for a process for preparation of acetals, particularly MDBS and DMDBS which does not employ any expensive solvents or mineral acids.

DEFINITIONS

As used in the present specification, the following words and phrases are generally intended to have the meanings as set forth below, except to the extent that the context in which they are used indicates otherwise.

The phrase "ionic fluid" is used herein to refer to an in situ formed solvated ionic compound in a solvent. The ionic fluid essentially comprises an entity formed by hydrogen bonding between a quaternary ammonium compound and a hydrogen donor compound in the presence of a solvent.

OBJECTS OF THE INVENTION

It is an object of the present invention to provide a process for preparation of alditol acetal derivative compounds in high yields and purity.

It is another object of the present invention to provide a process that allows the preparation of symmetrical and asymmetrical DibenzylideneSorbitol compounds without any limitation.

It is still another object of the present invention to provide a process for preparation of acetal derivatives which is economical.

It is yet another object of the present invention to provide a process for preparation of acetal derivatives which is environment friendly.

It is yet another object of the present invention to provide a process for preparation of acetal derivatives which employs a single recyclable solvent having ionic compound formed in situ (ionic fluid).

It is yet another object of the present invention to provide a process for preparation of acetal derivatives wherein there the final product is devoid of any residual free acid.

It is yet another object of the present invention to provide a process for preparation of acetal derivatives which is safe.

It is a further object of the invention to provide a method which allows the production of monoacetal and diacetal derivatives without the formation of triacetal derivates.

SUMMARY OF INVENTION

In accordance with a first aspect of the present invention, there is provided a process for preparation of acetal derivatives selected from the group consisting of DMDBS (1,3:2,4-bis(3,4-dimethylbenzylidene)sorbitol) and MDBS (1,3:2,4-bis(4-methylbenzylidene)sorbitol) comprising the following steps:
- preparing a quaternary ammonium salt based ionic fluid;
- carrying out a dehydrocondensation reaction by adding an aldehyde and an alditol in the mole ratio of 2:1 in the ionic fluid under continuous stirring to form a reaction mixture;
- stirring the reaction mixture to maintain the contents in a suspension form; and
- discontinuing the stirring of the reaction mixture to allow the mass formed in the reaction mixture to settle and separating the supernatant ionic fluid containing mother liquor;
- isolating and purifying the mass by filtering, washing and drying to obtain an acetal derivative without any free acid residue present therein.

Typically, the method step of preparing an ionic fluid comprises forming an in situ ionic compound in a solvent by adding a hydrogen donor and a 'quaternary ammonium salt' independently in equimolar quantities to the solvent.

In accordance with one of the embodiments the ionic fluid is prepared at a temperature in the range of about 25 to about 35° C.

Typically, the solvent is at least one selected from the group carboxylic acids, amides, alcohols, amines, ketones (aldehydes), asters, alkyl halides, ethers, aromatics for example; methanol, ethanol, propan-1-ol, propan-2-ol, 1-butanol, isobutanol, 2-butanol, tert-butanol, dichloromethane, tetrahydrofuran, methyl acetate, ethyl acetate, acetone, dimethylformamide, acetonitrile, dimethyl sulfoxide, formic acid, acetic acid, methyl ethyl ketone, dimethyl carbonate, diethyl ketone, acetic anhydride, acetone, tert-butyl methyl ether, diethyl amine, diethylene glycol, N,N-dimethylacetamide, diethylene glycol dimethyl ether, ethylene glycol dimethyl ether, ethylene glycol, glycerin, hexamethylphosphoramide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride, and water Typically, the hydrogen donor is selected from the group consisting of at least one acid selected from the group consisting of alkyl and aryl sulfonic acids, carboxylic acids, amides, ethers, esters, aldehydes, ketones, alcohols and carbohydrates for example sulfonic acid, methanesulfonic acid, ethanesulfonic acid, 1-propanesulfonicacid, benzenesulfonic acid, butanesulfonic acid, decane sulfonic acid, dodecane sulfonic acid, heptane sulfonic acid, hexanesulfonic acid, octane sulfonic acid, pentanesulfonic acid, O-toluenesulfonic acid, m-toluenesulfonic acid, p-toluenesulfonic acid, trifluromethane sulfonic acid, tri-chloromethane sulfonic acid, 3-methyl-1-butane sulfonic acid, 2-methyl-1-propane sulfonic acid, xylenesulfonic acid, oxalic acid, citric acid, benzoic acid, tartaric acid and maleic acid. In accordance with one embodiment, the hydrogen donor is PTSA (Para-toluenesulfonic acid).

Typically, the quaternary ammonium salt is choline chloride.

Alternatively, the ionic compound is prepared by reacting the equimolar quantities of para-toluene sulfonic acid and choline chloride at a temperature of 50° C. Typically, the ionic compound is formed by the hydrogen bonding between a quaternary ammonium salt and at least one hydrogen donor selected from the group consisting of alkyl and aryl sulfonic acids, carboxylic acids, amides, ethers, esters, aldehydes, ketones, alcohols and carbohydrates.

Typically, the ionic fluid acts as an acid catalyst that does not lead to the formation of acidic residues in the reaction mixture. Typically, the ionic fluid acts as a reaction medium.

Typically, the dehydrocondensation reaction is carried out at a temperature in the range of about 25° C. to about 50° C.

In accordance with a second aspect of the present invention, there is provided a process for preparation of acetal derivatives selected from the group consisting of DMDBS (1,3:2,4-bis(3,4-dimethylbenzylidene)sorbitol) and MDBS (1,3:2,4-bis(4-methylbenzylidene)sorbitol) comprising the following steps:
- preparing a quaternary ammonium salt based ionic liquid;
- carrying out a dehydrocondensation reaction by adding an aldehyde and an alditol in a mole ratio of 2:1 in the ionic liquid under continuous stirring to form a reaction mixture;
- stirring the resultant reaction mixture to maintain the contents in a suspension form; and
- discontinuing the stirring of the reaction mixture to allow the mass formed in the reaction mixture to settle and separating the supernatant mother liquor containing the ionic liquid;
- isolating and purifying the mass by filtering, washing and drying to obtain an acetal derivative without any free acid residue present therein.

Typically, the quaternary ammonium based ionic liquid is prepared by heating choline chloride and para-toluene sulfonic acid together.

Typically, the ionic liquid acts as a catalyst and a medium for the dehydrocondensation reaction wherein the end product is devoid of any acidic residue.

Typically, the aldehyde is at least one aldehyde selected from the group consisting of unsubstituted benzaldehyde, and substituted aldehydes including benzaldehyde, 4-methylbenzaldehyde, 3-methylbenzaldehyde, 4-propylbenzaldehyde, p-ethylbenzaldehyde, 4-butylbenzaldehyde, 4-lsopropylbenzaldehyde, 4-isobutylbenzaldehyde, 2,4-dimethylbenzaldehyde, 3,4-dimethylbenzaldehyde, 3,5-dimethylbenzaldehyde, 3-methyl-4-methoxybenzaldehyde, 2,4,5- trimethylbenzaldehyde, 3-hex-1-ynylbenzaldehyde, piperonal, 3-hydroxy-5,6,7,8-tetrahydro-2-naphthaldehyde, 3-Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde, 4-fluoro-3-methyl-, 5,6,7,8-tetrahydro-2-naphthaldehyde, 4-fluoro-3,5-dimethylbenzaldehyde, 4-(trifluoromethyl)benzaldehyde, 3-bromo-4-ethoxybenzaldehyde and mixtures thereof.

Typically, the alditol is selected from the group consisting of sorbitol (100%) and iso-propyl sorbitol. Alternatively, the alditol is an aqueous solution of sorbitol with a concentration in the range of about 40% to about 99%.

Typically, the method step of stirring is carried out for a period in the range of about 100 to 800 rpm. Typically, the mother liquor is recycled for carrying out the dehydrocondensation reaction for at least 35 cycles, preferably 30 cycles.

DETAIL DESCRIPTION OF INVENTION

In order to overcome the shortcomings of the hitherto reported processes which employ expensive solvents or mineral acid catalysts and moderate temperatures for the preparation of acetals, the inventors of the present invention have chosen the specific ionic fluids for the preparation of the acetals, particularly MDBS and DMDBS.

Using the ionic compounds as taught in U.S. Pat. No. 7,183,433 directly for any chemical synthesis as catalyst and solvent or solvent alone demands high energy in any chemical synthesis process. Still furthermore, product separation remains a major issue in case of reactions that employs ionic compound. Ionic compounds have the ability to dissolve wide variety of substances and isolation of a particular product may be very difficult at times.

The process in accordance with the present invention overcomes the above mentioned limitations associated with the use of ionic liquids. The process in accordance with the present invention does not require high amounts of energy since it is carried out at a temperature that is lower than 50° C.

In a first aspect of the present invention there is provided a process for preparation of acetal derivatives particularly, MDBS and DMDBS by dehydrocondensation reaction between an aldehyde and alditol using an ionic fluid at a relatively low temperature under atmospheric pressure, comprising the following steps:
    preparing a quaternary ammonium salt based ionic fluid;
    carrying out a dehydrocondensation reaction by adding an aldehyde and an alditol in a mole ratio of 2:1 in the ionic fluid under continuous stirring to form a reaction mixture;
    stirring the resultant reaction mixture to maintain the contents in a suspension form; and
    discontinuing the stirring of the reaction mixture to allow the mass formed in the reaction mixture to settle and separating the supernatant ionic fluid containing mother liquor;
    isolating and purifying the mass by filtering, washing and drying to obtain an acetal derivative without any free acid residue present therein.

The inventors of the present invention have found out a simple process for preparation of solvated ionic fluid which obviates the need for high temperature, particularly beyond 50° C. and which is faster than the process reported in U.S. Pat. No. 7,183,433.

In accordance with the present invention, the ionic fluids are formed in situ upon the addition of equimolar quantities of a quaternary ammonium salt having a general formula $R1R2R3R4N^+X^-$ and a hydrogen donor compound in a solvent independently. Typically, the solvent is selected from the group carboxylic acids, amides, alcohols, amines, ketones (aldehydes), asters, alkyl halides, ethers, aromatics for example; methanol, ethanol, propan-1-ol, propan-2-ol, 1-butanol, isobutanol, 2-butanol, tert-butanol, dichloromethane, tetrahydrofuran, methyl acetate, ethyl acetate, acetone, dimethylformamide, acetonitrile, dimethyl sulfoxide, formic acid, acetic acid, methyl ethyl ketone, dimethyl carbonate, diethyl ketone, acetic anhydride, acetone, tert-butyl methyl ether, diethyl amine, diethylene glycol, N,N-dimethylacetamide, diethylene glycol dimethyl ether, ethylene glycol dimethyl ether, ethylene glycol, glycerin, hexamethylphosphoramide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride, and water.

In one of the embodiments, the ionic fluid is prepared by independently adding 0.1 mole choline chloride and para toluene sulfonic acid in a solvent under continuous stirring at a room temperature.

There are several advantages associated with the method step of forming the ionic fluid in situ in accordance with the present invention. One key advantage of the method step of preparing an ionic fluid in accordance with the present invention is that unlike the prior art process reported in U.S. Pat. No. 7,183,433, it is carried out at low temperature thereby saving the energy. Furthermore, it also saves the time required in preparation of the ionic fluid. Still furthermore, the in situ ionic compound preparation in a solvent eliminates the separate eutectic ionic compound preparation step.

The in situ formation of the ionic compound is the result of formation of hydrogen bonds between the anion of the salt and the hydrogen donor compound in the solvent. Ionic compounds comprise nano-structures with an extended network of cations and anions connected together by hydrogen bonds. Self diffusion co-efficient of these nano-structures is higher when the ionic compound is in a dissolved state in the solvent.

The hydrogen donors are typically selected from a group of compounds consisting of alkyl and aryl sulfonic acids, carboxylic acids, amides, ethers, esters, aldehydes, ketones, alcohols and carbohydrates for example sulfonic acid, methanesulfonic acid, ethanesulfonic acid, 1-propanesulfonicacid, benzenesulfonic acid, butanesulfonic acid, decane sulfonic acid, dodecane sulfonic acid, heptane sulfonic acid, hexanesulfonic acid, octane sulfonic acid, pentanesulfonic acid, O-toluenesulfonic acid, m-toluenesulfonic acid, p-toluenesulfonic acid, tri-fluromethane sulfonic acid, tri-chloromethane sulfonic acid, 3-methyl-1-butane sulfonic acid, 2-methyl-1-propane sulfonic acid, xylenesulfonic acid, oxalic acid, citric acid, benzoic acid, tartaric acid and maleic acid. while the anions quaternary ammonium compound of the formula $R1R2R3R4N^+X^-$ are selected from the consisting of chloride, nitrate and tetraborate.

The inventors of the present invention have found that the ionic fluid comprising an in situ formed ionic compound prepared by the process in accordance with the present invention possesses the same physico-chemical characteristics as shown by an ionic fluid formed by dissolving a pre-prepared ionic compound in a solvent.

The ionic compound formation by result of cations and anions connection by hydrogen bond were reported to have supramolecular structural organization (Olivier-Bourbigou, H., et al., Applied Catalysis A: General, 373, 1-56, 2010; Deetlefs, M., et al., J. Physical Chemistry B. 110, 12055-12061, 2006; Canongia Lopez, J. N. and Padua, A. A. H., J. Physical Chemistry B. 110, 3330-3335, 2006). The continuous microdomains structure formed due to the network of hydrogen bond seem to be favorable for catalytic reactions since acid is not available in free form and this will not impart any residual acidity to the final product.

In accordance with the process of the present invention, the dehydrocondensation reaction is typically carried out using the ionic fluid which acts as a solvent, and/or catalyst. Typically, the dehydrocondensation reaction is carried out at a temperature in the range about 25 to about 50° C.

In accordance with a second aspect of the present invention, there is provided a process for preparation of acetal derivatives selected from the group consisting of DMDBS (1,3:2,4-bis(3,4-dimethylbenzylidene)sorbitol) and MDBS (1,3:2,4-bis(4-methylbenzylidene)sorbitol) comprising the following steps:

preparing a quaternary ammonium salt based ionic liquid;

carrying out a dehydrocondensation reaction by adding an aldehyde and an alditol in a mole ratio of 2:1 in the ionic liquid under continuous stirring to form a reaction mixture;

stirring the resultant reaction mixture to maintain the contents in a suspension form; and discontinuing the stirring of the reaction mixture to allow the mass formed in the reaction mixture to settle and separating the supernatant mother liquor containing the ionic liquid;

isolating and purifying the mass by filtering, washing and drying to obtain an acetal derivative without any free acid residue present therein.

Typically, the quaternary ammonium based ionic liquid is prepared by heating choline chloride and para-toluene sulfonic acid together.

Typically, the ionic liquid acts as a catalyst and a medium for the dehydrocondensation reaction wherein the end product is devoid of any acidic residue.

The aldehyde employed in the process of the present invention is at least one selected from the group consisting of unsubstituted benzaldehyde, and substituted aldehydes including benzaldehyde, 4-methylbenzaldehyde, 3-methylbenzaldehyde, 4-propylbenzaldehyde, p-ethylbenzaldehyde, 4-butylbenzaldehyde, 4-Isopropylbenzaldehyde, 4-isobutylbenzaldehyde, 2,4-dimethylbenzaldehyde, 3,4-dimethylbenzaldehyde, 3,5-dimethylbenzaldehyde, 3-methyl-4-methoxybenzaldehyde, 2,4,5-trimethylbenzaldehyde, 3-hex-1-ynylbenzaldehyde, piperonal, 3-hydroxy-5,6,7,8-tetrahydro-2-naphthaldehyde, 3-Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-Propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde, 4-fluoro-3-methyl-, 5,6,7,8-tetrahydro-2-naphthaldehyde, 4-fluoro-3,5-dimethylbenzaldehyde, 4-(trifluoromethyl)benzaldehyde, 3-bromo-4-ethoxybenzaldehyde and mixtures of thereof.

Typically, the alditol used in accordance with the process of the present invention is selected from the group consisting of sorbitol (100%) and iso-propyl sorbitol. Alternatively, an aqueous solution of sorbitol with a concentration in the range of about 40% to about 99% is used as the alditol.

The catalytic activity of the ionic fluid depends on hydrogen donor capability of the acid used for preparation of the ionic fluid. Accordingly, the catalytic activity of the ionic fluids varies depending on the type of acid used in following order: Methanesulfonic Acid>Para ToluenSulfonic Acid>Oxalic Acid>Maleic Acid>Citirc Acid. Catalytic activity of the ionic fluids which comprise stronger acids as the hydrogen donors is inversely proportional to the temperature at which the reaction is carried out. However, if the ionic fluids comprising weak acids as hydrogen donors are employed then their catalytic activity is in direct proportion to the temperature.

The catalytic activity in the wide range of temperatures depends on the salt that is forming ionic compound with hydrogen bond donor indicating the stability and strength of the hydrogen bond (Angew. Chem. Int. Ed., 2000, 39, 3772-3789, Ionic Liquids—New "Solutions" for Transition Metal Catalysis).

The inventors of the present invention have surprisingly found out that the product obtained by the process of the present invention is completely free of any residual free acid. The residual free acid in the product is highly undesirable since it promotes the hydrolysis of the end product at high temperatures, especially during the drying process.

The process of the present invention is therefore particularly advantageous since it obviates the need for neutralizing residual free acid in the end product thereby adding to the cost and complexity of the process. This demonstrates the utility of the ionic fluids as a reaction medium to carry out the acid based dehydrocondensation reactions.

In accordance with process of the present invention the mother liquor is recyclable and is used as such for carrying out the dehydrocondensation reaction. It has been found by the inventors of the present invention that the mother liquor retains its catalytic activity without compromising the yield and the purity of the end product even after recycling at least 35 times, preferably 30 times. In fact, with every recycle, the mother liquor causes a marginal increase in the yield on account of the presence of excess amount of aldehyde either in the mono intermediate or free form.

The following examples further illustrate the present invention but are not to be construed as limiting the invention as defined in the claims appended hereto.

Example 1

Toluene-4-sulphonic acid monohydrate (PTSA), a hydrogen donor (51.8 gms) was reacted with choline chloride (38.2 gms) in equal mole ratio to prepare deep eutectic ionic compound. The temperature had to be raised to 50° C. to obtain the clear liquid and then cooled. The ionic compound obtained was used as solvent and catalyst for carrying out the dehydration reaction at room temperature, for example 3,4 dimethyl benzaldehyde was reacted with sorbitol to form acetals of 1,3:2,4-bis(3,4-dimethylbenzylidene) sorbitol.

3,4 dimethyl benzaldehyde and sorbitol in 1:1 mole ratio were added to the ionic compound and stirred to initiate the reaction. The solid mass formed within few minutes of starting the reaction. The stirring speed was increased to keep the mass in suspension condition and reaction was continued for 8 hrs. The solid product was filtered and washed with 250 ml diethylether. The white solid product was dried in oven at 95° C. for 2 hrs followed by air dried for 4 hrs for measuring the yield. The yield was found to be 75% with a purity of 37%.

Example 2

The choline chloride (1.4 gm) and PTSA (1.9 gms) were added to methanol (30 ml) and mixed well to prepare the ionic fluid. 3,4 dimethyl benzaldehyde (0.8 ml) and sorbitol (1.5 gm) were added to the ionic fluid and stirred to initiate the reaction at 26° C. The thick solid mass formed after few minutes of starting the reaction. The stirring speed was increased to keep the mass in suspension condition and reaction was continued for 8 hrs. The solid product was filtered and washed with 100 ml diethylether. The white solid product was dried in an oven at 95° C. for 2 hrs followed by air drying for 4 hrs for measuring the yield. The yield and purity were found to be 22% and 97.5% respectively.

Example 3

The choline chloride (0.21 gm) and PTSA (0.29 gm) were added to methanol (30 ml) and mixed well to prepare the ionic fluid. 3,4 dimethyl benzaldehyde (0.8 ml) and sorbitol (1.5 gm) were added to the ionic fluid and stirred to initiate the reaction. The reaction was continued for 8 hrs at 26° C. The solid product was filtered and washed with 100 ml diethylether. The white solid product was dried in oven at 95° C. for 2 hrs followed by air dried for 4 hrs for measuring the yield. The yield and purity were found to be 37% and 95.9% respectively.

Example 4

The procedure of example 1 was followed except, mole ratio of 3,4 dimethyl benzaldehyde to sorbitol was increased to 2:1. After few minutes, a thick white mass was formed and clogged the stirrer within an hour. However, reaction was allowed to continue for 8 hrs at 26° C. The yield and purity were found to be 70% and 43% respectively.

Example 5

The procedure of example 2 is followed except, mole ratio of 3,4 dimethyl benzaldehyde to sorbitol was increased to 2:1 and continued the reaction for 8 hrs at 26° C. The yield and purity were found to be 77% and 98.7% respectively.

Example 6

The procedure of example 3 is followed except, mole ratio of 3,4 dimethyl benzaldehyde to sorbitol was increased to 2:1 and continued the reaction for 8 hrs. at 26° C. The yield and purity were found to be 52.4% and 72% respectively.

Example 7

Oxalic acid dihydrate, a hydrogen donor (28.5 gms) was mixed and allowed to react with choline chloride (61.5 gms). The mixture is stirred well at 65° C. until a uniform clear liquid is obtained. The procedure of example 4 was followed except oxalic acid was used in place of PTSA and the reaction was continued for 8 hrs. The yield and purity were found to be 58% and 98% respectively.

Example 8

The choline chloride (1.4 gm) and oxalic acid (0.65 gms) were added to methanol (30 ml) and mixed well to prepare the ionic fluid. 3,4 dimethyl benzaldehyde (1.5 ml) and sorbitol (1.5 gm) were added to the ionic fluid and stirred to initiate the reaction at 26° C. The white solid product started appearing after 90 minutes of reaction and was continued for 8 hrs. The solid product was filtered and washed with 100 ml diethylether. The white solid product was dried in oven at 95° C. for 2 hrs followed by air dried for 4 hrs for measuring the yield. The yield and purity were found to be 24% and 69.8% respectively.

Example 9

The procedure of example 8 was followed with 0.35 gms of choline chloride and 0.15 gms oxalic acid adding to methanol (30 ml). The yield and purity were found to be 25.7% and 95.9% respectively.

Example 10

Citric acid, a hydrogen donor (3.5 gms) was reacted with choline chloride (7 gms) to prepare deep eutectic ionic compound. The mixture was stirred well at 65° C. until a uniform clear liquid is obtained. The ionic compound was cooled to room temperature to follow the procedure of example 4 and reaction did not take place.

Example 11

The choline chloride (1.4 gm) and citric acid (0.7 gms) were added to methanol (30 ml) and mixed well to prepare the ionic fluid. 3,4 dimethyl benzaldehyde (1.5 ml) and sorbitol (1.5 gm) were added to the ionic fluid and stirred to initiate the reaction. The reaction found to be very slow at 26° C. and reaction was stopped after 8 hrs. The solid product was filtered and washed with 100 ml diethylether. The white solid product was dried in oven at 95° C. for 2 hrs followed by air dried for 4 hrs for measuring the yield. The yield and purity were found to be 5.2% and 89.8% respectively.

Example 12

The choline chloride (0.33 gm) and citric acid (0.17 gms) were added to methanol (30 ml) and mixed well to prepare the ionic fluid. 3,4 dimethyl benzaldehyde (1.5 ml) and sorbitol (1.5 gm) were added to the ionic fluid and stirred to initiate the reaction. The reaction found to be very slow at 26° C. and reaction was stopped after 8 hrs. The solid product was filtered and washed with 100 ml diethylether. The white solid product was dried in oven at 95° C. for 2 hrs followed by air dried for 4 hrs for measuring the yield. The yield and purity were found to be 1.8% and 94.3% respectively.

Example 13

The choline chloride (1.4 gm) and methanesulfonicacid (MSA) (0.96 gms) were added to methanol (30 ml) and mixed well to prepare the ionic fluid. 3,4 dimethyl benzaldehyde (1.5 ml) and sorbitol (1.5 gm) were added to the ionic fluid and stirred to initiate the reaction at 26° C. The thick solid mass formed after few minutes of starting the reaction and the reaction was continued for 8 hrs. The solid product was filtered and washed with 100 ml diethylether. The white solid product was dried in oven at 95° C. for 2 hrs followed by air dried for 4 hrs for measuring the yield. The yield and purity were found to be 80% and 99.8% respectively.

Example 14

The procedure of example 5 was repeated except, the reaction temperature was maintained at 45° C. The yield and purity were found to be 70% and 97.5% respectively.

Example 15

The procedure of example 8 was repeated except, the reaction temperature was maintained at 45° C. The yield and purity were found to be 36.5% and 98.5% respectively.

Example 16

The procedure of example 11 was repeated except, the reaction temperature was maintained at 45° C. The yield and purity were found to be 10% and 98.2% respectively.

Example 17

The procedure of example 13 was repeated except, the reaction temperature was maintained at 45° C. The yield and purity were found to be 75% and 98.7% respectively.

Example 18

Example for Recycling/Reusing of Mother Liquor

The procedure of example 5 was followed except, the mother liquor obtained from example 5 was replenished with 3,4 dimethyl benzaldehyde and sorbitol in 2:1 mole ratio and continued the reaction. The yield and purity were found to be 100% and 97% respectively.

Example 19

Example for Recycling/Reusing of Mother Liquor

The procedure of example 5 was followed except, the mother liquor obtained from example 18 was replenished with 3,4 dimethyl benzaldehyde and sorbitol in 2:1 mole ratio and continued the reaction. The yield and purity were found to be 85% and 98.3% respectively.

Example 20

Example for Recycling/Reusing of Mother Liquor

The procedure of example 5 was followed except, the filtrate obtained from example 19 was replenished with 3,4 dimethyl benzaldehyde and sorbitol in 2:1 mole ratio and continued the reaction. The yield and purity were found to be 93% and 97.3% respectively.

Example 21

The procedure of example 5 was followed except, p-tolualdehyde was used in place of 3,4 dimethyl benzaldehyde. The product, 1,3:2,4-bis(4-methylbenzylidene) sorbitol yield was found to be 42.5% with 90.5% purity.

Example 22

The procedure of example 8 was followed except, p-tolualdehyde was used in place of 3,4 dimethyl benzaldehyde. The product, 1,3:2,4-bis(4-methylbenzylidene) sorbitol yield was found to be 40% with 90% purity.

Example 23

The procedure of example 11 was followed except, p-tolualdehyde was used in place of 3,4 dimethyl benzaldehyde. The product, 1,3:2,4-bis(4-methylbenzylidene) sorbitol yield was found to be 4% with 91% purity.

Example 24

The procedure of example 13 was followed except, p-tolualdehyde was used in place of 3,4 dimethyl benzaldehyde. The product, 1,3:2,4-bis(4-methylbenzylidene) sorbitol yield was found to be 55% with 91.5% purity.

Test Data:

Comparative Example

The process for preparing dibenzylidene sorbitol by a prior art process as disclosed in U.S. Pat. No. 4,429,140 was carried out to comparatively assess the energy requirement, time requirement and the overall complexity of the process in terms of the number of reagents used in the process in accordance with the present invention. 3,4 dimethyl benzaldehyde and sorbitol in 2.5:1 mole ratio were mixed in cyclohexane (100 weight parts) and methanol (100 weight parts mixed). To this mixture 98% sulfuric acid (0.5 weight parts) serving as catalyst was added and the dehydrocondensation reaction was carried out at 78 to 82° C. in the nitrogen atmosphere for 3 hours. The water formed during the reaction was continuously distilled off as an azeotropic mixture along with cyclohexane and methanol. The cyclohexane condensed and separated off by the condenser, was recycled through the reaction system, while aqueous layer was withdrawn from the system. The reaction was completed after 3 hours cooled, neutralized with an aqueous KOH solution, washed with hot water and filtered to obtain white powder. Yield was 95% and purity was 97.5%.

It was found that the process in accordance of the present invention required less energy since it was carried out at room temperature. Furthermore, the process of the present invention also involved less number of method steps which did not require any of the harmful or corrosive chemical like sulfuric acid. Still furthermore, unlike the prior art process described herein above, the catalyst in the form of ionic fluid in case of the process of the present invention was recyclable thereby making the process environment friendly.

Test Examples

Use of PTSA and Methanesulfonic Acid as Acid Catalysts

The inventors of the present invention also carried out the dehydrocondensation reaction in solvent in the presence of methanesulfonic acid and para toluenesulfonic acid alone. It was found out that the mother liquor generated in such process could not be reused beyond two to three cycles. Furthermore, the end product had to be neutralized to remove the residual acidity.

Example 25

Reaction with Using PTSA Alone

PTSA (9.5 gms) was added to methanol (150 ml) and mixed well and 3,4 dimethyl benzaldehyde (7.5 ml) and sorbitol (5 gm) were added to the methanol solution and stirred to initiate the reaction at 26° C. The reaction was continued for 8 hrs. The solid product was filtered and mother liquor was collected for further reactions. Product was neutralized with aqueous solution of NaOH and followed by diethylether (100 ml) wash. The product was dried in oven at 95° C. for 2 hrs followed by air dried for 4 hrs for measuring the yield. The yield and purity were found to be 70% and 91.4% respectively.

Example 26

The procedure of example 25 was followed except, the mother liquor obtained from example 25 was replenished with 3,4 dimethyl benzaldehyde and sorbitol in 2:1 mole ratio and continued the reaction. The yield and purity were found to be 88% and 93% respectively.

Example 27

The procedure of example 25 was followed except, the mother liquor obtained from example 26 was replenished with 3,4 dimethyl benzaldehyde and sorbitol in 2:1 mole ratio and continued the reaction. The yield and purity were found to be 80% and 93% respectively.

Example 28

The procedure of example 25 was followed except, mother liquor obtained from example 27 was replenished with 3,4 dimethyl benzaldehyde and sorbitol in 2:1 mole ratio and continued the reaction. The yield and purity were found to be 60% and 94% respectively.

It was therefore confirmed that if the dehydrocondensation reaction is carried out using an acid (PTSA) alone, then the mother liquor resulting from such reaction cannot be re-circulated beyond 2 to 3 times.

While certain embodiments of the inventions have been described, these embodiments have been presented by way of example only, and are not intended to limit the scope of the inventions. Variations or modifications to the design and construction of this invention, within the scope of the invention, may occur to those skilled in the art upon reviewing the disclosure herein. Such variations or modifications are well within the spirit of this invention. The accompanying claims and their equivalents are intended to cover such forms or modifications as would fall within the scope and spirit of the invention.

The numerical values given for various physical parameters, dimensions and quantities are only approximate values and it is envisaged that the values higher than the numerical value assigned to the physical parameters, dimensions and quantities fall within the scope of the invention and the claims unless there is a statement in the specification to the contrary.

The invention claimed is:

1. A process for preparation of acetal derivatives selected from the group consisting of DMDBS (1,3:2,4-bis(3,4-dimethylbenzylidene)sorbitol) and MDBS (1,3:2,4-bis(4-methylbenzylidene) sorbitol) comprising the following steps:
preparing a quaternary ammonium salt based ionic fluid by adding a hydrogen donor and a 'quaternary ammonium salt' independently in equimolar quantities to at least one solvent;
carrying out a dehydrocondensation reaction by adding an aldehyde and an alditol in a mole ratio of 2:1 in the ionic fluid under continuous stirring to form a reaction mixture;
stirring the resultant reaction mixture to maintain the contents in a suspension form;
discontinuing the stirring of the reaction mixture to allow the mass formed in the reaction mixture to settle and separating the supernatant ionic fluid containing mother liquor; and
isolating and purifying the mass by filtering, washing and drying to obtain an acetal derivative without any free acid residue present therein.

2. A process as claimed in claim 1, wherein the ionic fluid is prepared by reacting the equimolar quantities of para-toluene sulfonic acid and choline chloride at a temperature in the range of about 15 to about 65° C.

3. A process as claimed in 1, wherein the solvent is at least one selected from the group of carboxylic acids, amides, alcohols, amines, ketones (aldehydes), asters, alkyl halides, ethers, and aromatics (methanol, ethanol, propan-1-ol, propan-2-ol, 1-butanol, isobutanol, 2-butanol, tert-butanol, dichloromethane, tetrahydrofuran, methyl acetate, ethyl acetate, acetone, dimethylformamide, acetonitrile, dimethyl sulfoxide, formic acid, acetic acid, methyl ethyl ketone, dimethyl carbonate, diethyl ketone, acetic anhydride, acetone, tert-butyl methyl ether, diethyl amine, diethylene glycol, N,N-dimethylacetamide, diethylene glycol dimethyl ether, ethylene glycol dimethyl ether, ethylene glycol, glycerin, hexamethylphosphoramide, hexamethylphosphorous triamide, isoamyl alcohol, 2-methoxyethanol, 2-methoxyethyl acetate, 1-methyl-2-pyrrolidinone, nitromethane, propanoic acid, pyridine, hydrogen fluoride, hydrogen chloride).

4. A process as claimed in claim 1, where in at least the hydrogen donor is selected from the group consisting of alkyl and aryl sulfonic acids, carboxylic acids, amides, ethers, esters, aldehydes, ketones, alcohols and carbohydrates (sulfonic acid, methanesulfonic acid, ethanesulfonic acid, 1-propanesulfonicacid, benzenesulfonic acid, butanesulfonic acid, decane sulfonic acid, dodecane sulfonic acid, heptane sulfonic acid, hexanesulfonic acid, octane sulfonic acid, pentanesulfonic acid, O-toluenesulfonic acid, m-toluenesulfonic acid, p-toluenesulfonic acid, tri-fluromethane sulfonic acid, tri-chloromethane sulfonic acid, 3-methyl-1-butane sulfonic acid, 2-methyl-1-propane sulfonic acid, xylenesulfonic acid, oxalic acid, citric acid, benzoic acid, tartaric acid and maleic acid.

5. A process as claimed in claim 1, wherein the quaternary ammonium salt is choline chloride.

6. A process as claimed in claim 1, wherein the ionic fluid is formed by reacting choline chloride and at least one hydrogen donor selected from the group of alkyl and aryl sulfonic acids, carboxylic acids, amides, ethers, esters, aldehydes, ketones, alcohols and carbohydrates (sulfonic acid, methanesulfonic acid, ethanesulfonic acid, 1-propanesulfonicacid, benzenesulfonic acid, butanesulfonic acid, decane sulfonic acid, dodecane sulfonic acid, heptane sulfonic acid, hexanesulfonic acid, octane sulfonic acid, pentanesulfonic acid, O-toluenesulfonic acid, m-toluenesulfonic acid, p-toluenesulfonic acid, tri-fluromethane sulfonic acid, tri-chloromethane sulfonic acid, 3-methyl-1-butane sulfonic acid, 2-methyl-1-propane sulfonic acid, xylenesulfonic acid, oxalic acid, citric acid, benzoic acid, tartaric acid and maleic acid.

7. A process as claimed in claim 1, wherein the dehydrocondensation reaction is carried out at a temperature in the range of about 25° C. to about 50° C.

8. A process as claimed in claim 1, wherein the ionic fluid is an acid catalyst and a medium for the dehydrocondensation reaction.

9. A process as claimed in claim 1, wherein the aldehyde is at least one aldehyde selected from the group of unsubstituted benzaldehyde, and substituted aldehydes including benzaldehyde, 4-methylbenzaldehyde, 3-methylbenzaldehyde, 4-propylbenzaldehyde, p-ethylbenzaldehyde, 4-butylbenzaldehyde, 4-lsopropylbenzaldehyde, 4-isobutylbenzaldehyde, 2,4-dimethylbenzaldehyde, 3,4-dimethylbenzaldehyde, 3,5-dimethylbenzaldehyde, 3-methyl-4-methoxybenzaldehyde, 2,4,5-trimethylbenzaldehyde, 3-hex-1-ynylbenzaldehyde, piperonal, 3-hydroxy-5,6,7,8-tetrahydro-2-naphthaldehyde, 3-Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-Propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde, 4-fluoro-3-methyl-, 5,6,7,8-tetrahydro-2-naphthaldehyde, 4-fluoro-3,5-dimethylbenzaldehyde, 4-(trifluoromethyl)benzaldehyde, 3-bromo-4-ethoxybenzaldehyde and mixtures thereof.

10. A process as claimed in claim 1, wherein the alditol is selected from the group of alditols consisting of sorbitol (100%) and iso-propyl sorbitol, preferably the alditol is an aqueous solution of sorbitol with a concentration in the range of about 40% to about 99%.

11. A process as claimed in claim 1, wherein the mother liquor is recycled for carrying out the dehydrocondensation reaction for at least 35 cycles.

12. A process as claimed in claim 1, wherein the quaternary ammonium based ionic fluid is prepared by heating choline chloride and para-toluene sulfonic acid together.

13. A process as claimed in claim 1, wherein the ionic fluid acts as a catalyst and a medium for the dehydrocondensation reaction.

14. A process as claimed in claim 1, wherein the mother liquor is recycled for carrying out the dehydrocondensation reaction for at least 30 cycles.

15. The process as claimed in claim 1, wherein the alditol is an aqueous solution of sorbitol with a concentration in the range of 40% to 99%.

* * * * *